United States Patent
Nishiuchi et al.

(10) Patent No.: US 7,439,528 B2
(45) Date of Patent: Oct. 21, 2008

(54) PARTICLE THERAPY SYSTEM AND METHOD

(75) Inventors: Hideaki Nishiuchi, Hitachinaka (JP); Katsuhisa Ike, Chiyoda (JP); Masumi Umezawa, Mito (JP); Koji Matsuda, Hitachi (JP)

(73) Assignee: Hitachi, Ltd., Tokyo (JP)

( * ) Notice: Subject to any disclaimer, the term of this patent is extended or adjusted under 35 U.S.C. 154(b) by 316 days.

(21) Appl. No.: 10/981,505

(22) Filed: Nov. 5, 2004

(65) Prior Publication Data

US 2005/0099145 A1    May 12, 2005

(30) Foreign Application Priority Data

Nov. 7, 2003 (JP) .............................. 2003-377672

(51) Int. Cl.
*A61N 5/00* (2006.01)
(52) U.S. Cl. ................................. 250/492.3; 250/492.1
(58) Field of Classification Search .... 250/492.1–492.3
See application file for complete search history.

(56) References Cited

U.S. PATENT DOCUMENTS

| | | | |
|---|---|---|---|
| 4,812,774 A * | 3/1989 | Tsumaki et al. ............. | 315/501 |
| 5,459,393 A | 10/1995 | Tanaka et al. | |
| 5,698,954 A * | 12/1997 | Hirota et al. ................. | 315/503 |
| 5,783,914 A * | 7/1998 | Hiramoto et al. ............ | 315/504 |
| 5,969,367 A * | 10/1999 | Hiramoto et al. ......... | 250/492.3 |
| 6,207,952 B1 | 3/2001 | Kan et al. | |
| 6,316,776 B1 * | 11/2001 | Hiramoto et al. ......... | 250/492.3 |
| 6,462,490 B1 * | 10/2002 | Matsuda et al. ............. | 315/507 |
| 2005/0087700 A1 * | 4/2005 | Tadokoro et al. ........ | 250/492.21 |

FOREIGN PATENT DOCUMENTS

| | | |
|---|---|---|
| JP | 06-076999 | 3/1994 |
| JP | 8-148298 | 6/1996 |
| JP | 09092500 | 4/1997 |

(Continued)

OTHER PUBLICATIONS

Rev. Sci. Instrum., vol. 64, No. 8, Aug. 1993, Light-ion beams for cancer, pp. 2079-2093.

*Primary Examiner*—Jack I Berman
*Assistant Examiner*—Andrew Smyth
(74) *Attorney, Agent, or Firm*—Dickstein Shapiro LLP

(57) ABSTRACT

A particle therapy system capable of confirming energy of an accelerated charged particle beam before the charged particle beam is irradiated to an irradiation target. A beam position monitor is disposed in a synchrotron, and a cavity voltage monitor is associated with an RF cavity for acceleration. An ion beam orbiting within the synchrotron is accelerated with application of an RF voltage applied to the RF cavity and is extracted from the synchrotron with application of an RF voltage applied to an RF knockout electrode. Based on a cavity voltage signal detected by the cavity voltage monitor, a frequency counter measures the frequency of the RF voltage applied to the RF cavity. Based on a voltage detected by the beam position monitor, a beam signal processing unit measures the position of a beam orbit. Based on the frequency of the RF voltage and the position of the beam orbit, the energy judgment processing unit determines whether energy of the ion beam after the end of the acceleration is normal or abnormal.

31 Claims, 11 Drawing Sheets

FOREIGN PATENT DOCUMENTS

| | | |
|---|---|---|
| JP | 10-118204 | 5/1998 |
| JP | 10-294200 | 11/1998 |
| JP | 11-64530 | 3/1999 |
| JP | 2001-043999 | 2/2001 |
| JP | 2002-151300 | 5/2002 |
| JP | 2002-217000 | 8/2002 |
| JP | 2002-367800 | 12/2002 |

* cited by examiner

PARTICLE THERAPY SYSTEM AND METHOD

BACKGROUND OF THE INVENTION

1. Field of the Invention

The present invention relates to a particle therapy system, and more particularly to a particle therapy system suitable for accelerating an ion beam, such as a proton or heavy ion beam, by an accelerator to be used in medical treatment.

2. Description of the Related Art

A particle therapy system employing an ion beam, such as a proton or heavy ion beam (hereinafter referred to also simply as a "beam"), for treatment of cancers is designed to be able to irradiate the beam in match with the shape of a diseased part in the body of a patient so that the beam is concentrated to the diseased part. In particular, adjustment of the beam range in the direction of depth from the body surface of the patient can be realized by adjusting energy of the beam.

A typical example of accelerators used in the particle therapy system is a synchrotron. The synchrotron has an RF cavity for acceleration (hereinafter referred to as an "RF cavity") in which an RF voltage is applied to an orbiting beam and the beam is accelerated to a desired level of energy. The beam having been accelerated to the desired level of energy is extracted from the synchrotron, is introduced to an irradiation apparatus through a beam transportation line, and is irradiated to the diseased part (cancer) in the body of the patient lying on a treatment couch.

The irradiation apparatus produces a beam in match with the size of the cancer and the depth thereof from the body surface of the patient, and then irradiates the produced beam. In general, the irradiation apparatus is constructed to be able to irradiate the beam based on one of known beam irradiation methods, i.e., a double scattering method (p. 2081 and FIG. 35 of Non-Patent Reference 1; "REVIEW OF SCIENTIFIC INSTRUMENTS", Vol. 64, No. 8 (August 1993), pp. 2079-2093), a wobbling method (p. 2084 and FIG. 41 of Non-Patent Reference 1), and an ion beam scanning method (Patent Reference 1; JP,A 10-118240 and pp. 2092-2093 of Non-Patent Reference 1).

Regardless of which one of those beam irradiation methods is utilized, the synchrotron constituting the accelerator of the particle therapy system is required to control energy of the extracted beam to a set energy level with high accuracy. To that end, the beam energy requires to be measured with high accuracy. It has hitherto been known to measure the beam energy by employing a water phantom disclosed in Patent Reference 2; JP,A 11-64530 and a multi-leaf Faraday cup described in Non-Patent Reference 2; "BEAM COMMISSIONING OF THE NEW PROTON THERAPY SYSTEM FOR UNIVERSITY OF TSUKUBA", M. Umezawa, et al., Proceedings of 2001 Particle Accelerator Conference, Chicago, USA (2001)).

SUMMARY OF THE INVENTION

Because the measurement of the beam energy employing the water phantom and the multi-leaf Faraday cup is performed in the state that the beam irradiated to the patient is shut off, the beam energy cannot be measured, as the occasion requires, while the beam is irradiated to the patient. In connection with the case of employing the beam scanning method, particularly, Patent Reference 1 proposes a method of dividing the diseased part into a plurality of layers in the direction of depth from the body surface of the patient and scanning the beam for each of the divided layers. To irradiate the beam to a certain layer, the beam energy is adjusted so that the beam reaches just the relevant layer. If the irradiated beam energy differs from a predetermined level of beam energy, the beam is irradiated to other layer than the relevant layer. From the viewpoint of avoiding such a trouble, it is desired to measure the ion beam before the ion beam is irradiated to the patient after the acceleration of the ion beam has ended.

An object of the present invention is to provide a particle therapy system capable of confirming energy of an accelerated charged particle beam before the charged particle beam is irradiated to an irradiation target.

To achieve the above object, the particle therapy system of the present invention is featured in comprising an energy determination device for determining energy of a charged particle beam orbiting within a circular accelerator after the end of acceleration of the charged particle beam by a circular accelerator. Since the energy determination device determines the energy of the charged particle beam orbiting within the circular accelerator after the end of the acceleration, the energy of the charged particle beam can be confirmed before the charged particle beam is irradiated to the irradiation target.

Preferably, the particle therapy system further comprises a beam intensity determination device for determining beam intensity of the charged particle beam orbiting within the circular accelerator after the end of acceleration of the charged particle beam by the circular accelerator. With this feature, the strength of the charged particle beam can be confirmed before the charged particle beam is irradiated to the irradiation target.

Preferably, the energy determination device determines that the energy of the charged particle beam orbiting after the end of the acceleration is normal, when a frequency of a radio frequency (RF) wave (e.g., an RF voltage) applied to an RF cavity for acceleration is within a first allowable range after the end of the acceleration and an orbit position of the orbiting charged particle beam after the end of the acceleration is within a second allowable range.

The charged particle beam orbiting within the circular accelerator is accelerated only when the relationship between the strength of a bending magnetic field and the revolution frequency of the charged particle beam is a predetermined one. Therefore, the energy of the charged particle beam orbiting after the end of the acceleration can be decided if the strength of the bending magnetic field and the revolution frequency of the charged particle beam are known. Also, the strength of the bending magnetic field affects the beam orbit position of the orbiting charged particle beam, and the frequency of the RF wave applied to the charged particle beam for accelerating the same is related to the revolution frequency of the charged particle beam. Accordingly, the energy of the charged particle beam orbiting after the end of the acceleration can be determined based on the frequency of the RF wave applied for acceleration and the orbit position of the charged particle beam.

Preferably, the energy determination device determines that the energy of the charged particle beam orbiting after the end of the acceleration is abnormal (differs from a predetermined level of energy), when the frequency of the RF wave after the end of the acceleration is outside the first allowable range and the orbit position of the orbiting charged particle beam after the end of the acceleration is outside the second allowable range.

Preferably, the energy determination device determines that the energy of the charged particle beam orbiting after the end of the acceleration is normal, when the strength of the bending magnetic field produced by a bending magnet is within a first allowable range and the orbit position of the orbiting charged particle beam is within the second allowable range. As mentioned above, the energy of the charged particle beam orbiting after the end of the acceleration can be decided if the strength of the bending magnetic field and the revolution frequency of the charged particle beam are known. Accordingly, the energy of the charged particle beam orbiting after the end of the acceleration can be determined based on the strength of the bending magnetic field and the frequency of the RF wave applied for acceleration.

Preferably, the particle therapy system further comprises a first safety device for permitting extraction of the charged particle beam from the circular accelerator when the energy determination device determines that the energy of the orbiting charged particle beam is normal, and for inhibiting extraction of the charged particle beam from the circular accelerator when the energy determination device determines that the energy of the orbiting charged particle beam is abnormal. With this feature, because the charged particle beam having energy at an abnormal level can be prevented from being irradiated to the irradiation target, it is possible to avoid irradiation of the charged particle beam to an unintended position (i.e., a position not set in a treatment plan) in the direction of depth of the irradiation target.

Preferably, the particle therapy system further comprises a second safety device for permitting extraction of the charged particle beam from the circular accelerator when the beam intensity determination device determines that the beam intensity of the orbiting charged particle beam is normal, and for inhibiting extraction of the charged particle beam from the circular accelerator when the beam intensity determination device determines that the beam intensity of the orbiting charged particle beam is abnormal. With this feature, in irradiation based on the ion beam scanning method, it is possible to suppress the charged particle beam from being irradiated at an excessive dose in a local area, and to make even the dose of the charged particle beam irradiated to a cancer in accordance with the treatment plan.

According to the present invention, the energy of the accelerated charged particle beam can be confirmed before the charged particle beam is irradiated to the irradiation target.

BRIEF DESCRIPTION OF THE DRAWINGS

FIGS. 4A and 4B show the operation of a synchrotron, in which FIG. 4A is a graph for explaining details of the operation and FIG. 4B is a chart for explaining details of an energy check stage in FIG. 4A;

DESCRIPTION OF THE PREFERRED EMBODIMENTS

Preferred embodiments of the present invention will be described below.

First Embodiment

Figure 1:
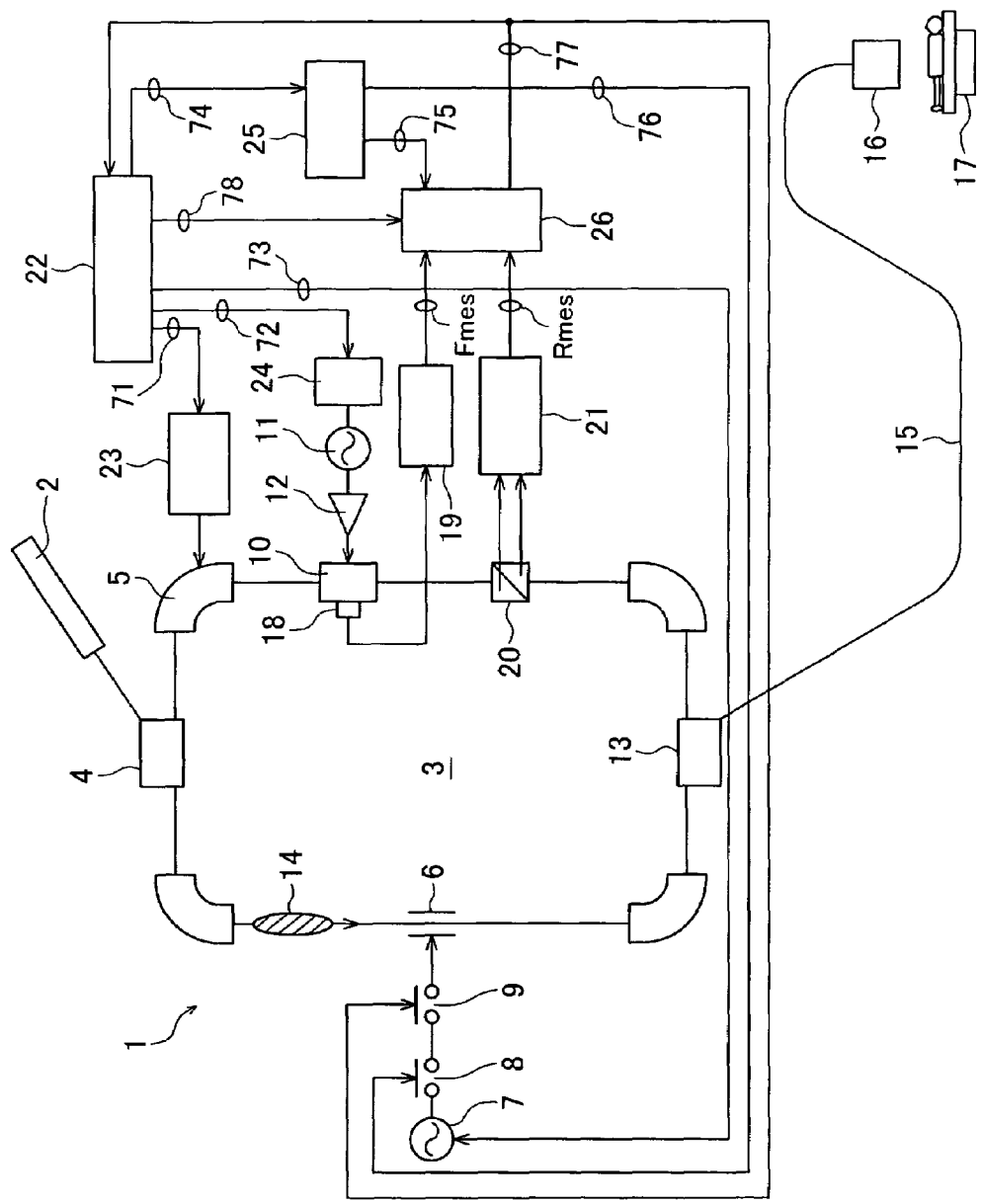
FIG. 1 is a block diagram of a particle therapy system according to one preferable embodiment, i.e., a first embodiment, of the present invention.
Figure 2:
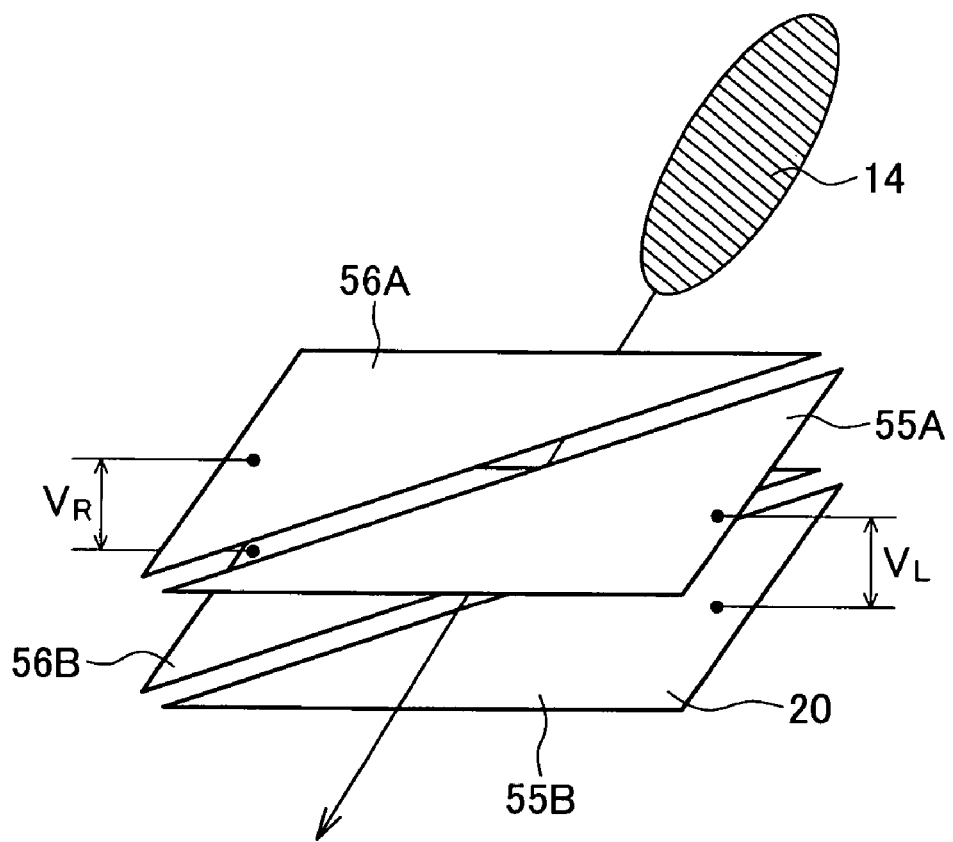
FIG. 2 is an illustration showing a beam position monitor in FIG. 1.

A particle therapy system according to a first embodiment of the present invention will be described with reference to FIG. 1. A particle therapy system 1 of this first embodiment comprises a synchrotron 3 constituting a circular accelerator, a beam transportation system 15, and an irradiation field forming apparatus (charged particle beam irradiation apparatus) 16. The irradiation field forming apparatus will be referred to as an "irradiation apparatus" hereinafter. The synchrotron 3 comprises an injection device 4, a plurality of bending magnets 5, an RF knockout electrode 6, an RF cavity 10 for acceleration, and a beam extraction deflector 13, which are installed along a beam orbit. Though not shown, a plurality of quadrupole magnets are also installed in the synchrotron 3. A magnet power supply 23 is connected to the bending magnets 5. The RF knockout electrode 6 is connected to an RF oscillator (RF power supply) 7 through an extraction switch (first on/off device) 8 and a gate switch (second on/off device) 9 serving as a first safety device. The RF oscillator 7 serves as an RF oscillator for beam extraction. Another RF oscillator 11 applies a predetermined RF voltage to the RF cavity 10 through a power amplifier 12 under control of an RF controller 24. The RF oscillator 11 serves as an RF oscillator for beam acceleration. A cavity voltage monitor 18 associated with the RF cavity 10 is connected to a frequency counter 19. A beam position monitor 20 disposed in the synchrotron 3 is connected to a beam signal processing unit (radial beam position measuring device) 21. As shown in FIG. 2, the beam position monitor 20 has two sets of electrodes each in the form of a triangular flat plate. One set is constructed of two electrodes 55A, 55B arranged opposite to each other with the beam orbit passing between them, and the other set is constructed of two electrodes 56A, 56B arranged opposite to each other with the beam orbit passing between them. Those electrodes are all connected to the beam signal processing unit 21. The frequency counter 19 and the beam signal processing unit 21 are connected to an energy judgment processing unit 26. The energy judgment processing unit 26 is connected to an accelerator controller 22 and the gate switch 9. The accelerator controller 22 is in turn connected to a timing controller 25, the energy judgment processing unit 26, the magnet power supply 23, and the RF controller 24. The timing controller 25 is connected to the energy judgment processing unit 26 and the extraction switch 8.

The accelerator controller 22 and the timing controller 25 serve as control units for supervising the various units of the synchrotron 3. The accelerator controller 22 manages control setting values for the relevant units, and the timing controller 25 manages timings in operations of the relevant units.

Figure 4A:
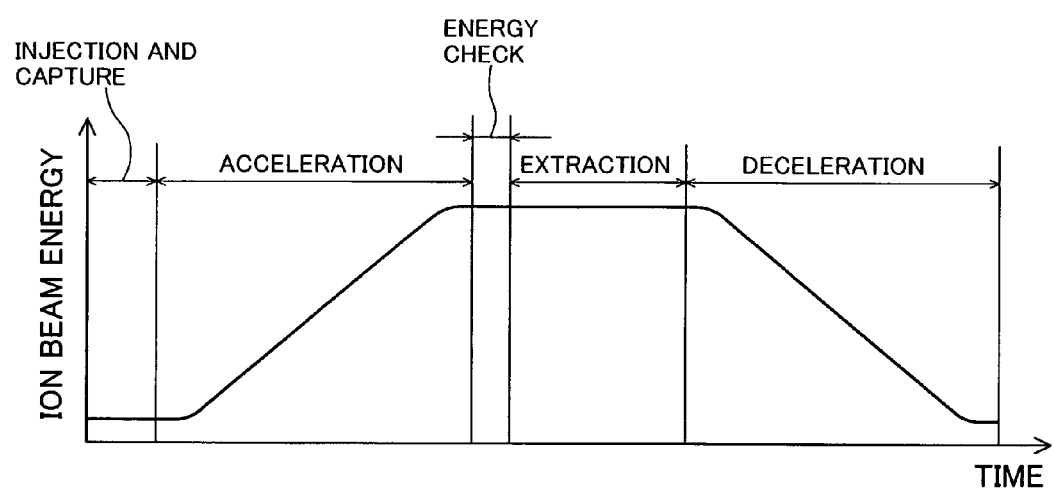

An outline of cancer treatment employing the particle therapy system 1 will be described below. As shown in FIG. 4A, the synchrotron 3 is operated by repeating successive stages of injecting and capturing an ion beam (heavy particle beam such as a proton beam or a carbon ion beam), i.e., a charged particle beam, accelerating the ion beam to a set level of energy, extracting the ion beam having reached the set level of energy, and decelerating the ion beam. Operation timings of those control stages of injection-and-capture, acceleration, extraction, and deceleration are defined depending on the energy to which the ion beam is to be accelerated. A time of the injection and capture stage is always constant regardless of a required level of the accelerated beam energy. Also, when the ion beam is accelerated and decelerated at a constant gradient regardless of the energy level, respective times of the acceleration and deceleration stages are prolonged as the energy level increases. Therefore, if a time allocated for each of repeated control cycles from the injection to the deceleration is defined, an extraction time is uniquely decided depending on the injection-and-capture time and the acceleration and deceleration times. Further, by setting the output timing of an energy check signal 75 to a point in time after the end of acceleration control, but before the start of extraction control, the energy level can be confirmed prior to the supply of the ion beam to the irradiation apparatus.

The required level of energy of the ion beam irradiated to the cancer in the body of a patient lying on a treatment couch 17 is decided depending on the depth of the cancer from the body surface of the patient. The energy at that required level represents energy of the ion beam after the end of acceleration by the synchrotron 3 (referred to as "set energy" herein), and is decided in a treatment planning stage performed before the start of the relevant treatment. The accelerator controller 22 takes in information of the set energy for the relevant patient from a treatment-plan information memory (not shown). In accordance with the operation pattern of the synchrotron 3, shown in FIG. 4A, which is decided based on the taken-in set energy information, the accelerator controller 22 outputs, to the timing controller 25, operation timing information 74 for the relevant units constituting the synchrotron 3. Further, to control the magnetic field strength of the bending magnets 5 (i.e., the bending magnet field strength) and the frequency of the RF voltage applied to the RF cavity 10, the accelerator controller 22 outputs, to the magnet power supply 23, a control command 71 for setting an operation pattern of the magnet power supply 23 and, to the RF controller 24, a control command 72 for setting an operation pattern of the RF oscillator 11. Also, the accelerator controller 22 sets, in the timing controller 25, control timing information 74 corresponding to the set energy of the ion beam after the end of the acceleration. In addition, corresponding to the set energy, the accelerator controller 22 sets, in the energy judgment processing unit 26, judgment information 78 such as the reference value of the beam orbit, the allowable range of an orbit deviation, the reference value of frequency of the RF voltage, and the allowable range of the frequency. Incidentally, the function of the energy judgment processing unit 26 may be incorporated an interlock controller (not shown) that serves as a safety device for the particle therapy system 1.

In operation, an ion beam 14 is first injected from a pre-accelerator 2 to the synchrotron 3. This embodiment uses a charged particle beam as the ion beam. When the ion beam is injected, the relevant magnet power supply 23 is controlled in accordance with the operation pattern set by the control command 71, and therefore the quadrupole magnets and the bending magnets 5 in the synchrotron 3 are excited by predetermined currents. Within the synchrotron 3, the ion beam 14 is closely concentrated with the RF voltage applied to the RF cavity 10. The application of the RF voltage to the RF cavity 10 is performed with control of the RF oscillator 11 performed by the RF controller 24 in accordance with the set operation pattern. The RF voltage from the RF oscillator 11 is amplified by the power amplifier 12 and then fed to the RF cavity 10. The close concentration of the ion beam 14 is realized by forming a region where the ion beam 14 can be stably accelerated (hereinafter referred to as an "RF bucket") with the RF voltage applied to the RF cavity 10. Such control for closely concentrating the beam is called RF capture, and the closely concentrated beam is called a bunched beam.

When accelerating the bunched ion beam 14, excitation currents applied to the quadrupole magnets and the bending magnets 5, i.e., the magnetic field strength, is increased by controlling the magnet power supply 23 in accordance with the set operation pattern until the energy of the orbiting ion beam reaches the set energy. Also, the frequency of the RF voltage applied to the RF cavity 10 is increased by controlling the RF oscillator 11 from the RF controller 24 in accordance with the set operation pattern. In other words, as the set magnetic field strength of the bending magnets 5 increases, the frequency of the RF voltage applied to the RF cavity 10 is increased. On that occasion, the magnet power supply 23 and the RF oscillator 11 are controlled in accordance with control commands from the accelerator controller 22 so that the predetermined relationship (expressed by Eq. (5) described later) is held between the bending magnetic field strength and the frequency of the RF voltage. As a result, the closely concentrated ion beam (bunched beam) 14 can be accelerated to the set energy while the bunched beam is caused to circulate within the synchrotron 3 along the orbit.

When an extraction permit signal 76 is outputted from the timing controller 25 after the energy of the orbiting ion beam has reached the set energy, the extraction switch 8 is closed and the RF signal outputted from the RF oscillator 7 is fed to the RF knockout electrode 6. At this time, the gate switch 9 is closed by an energy normal signal (described later) supplied from the energy judgment processing unit 26. When the RF signal is applied to the orbiting ion beam from the RF knockout electrode 6, the magnitude of betatron oscillation of the ion beam is so increased that the ion beam transits to the outside of the separatix and is extracted through the beam extraction deflector 13 (see Japanese Patent No. 2596292). The extracted ion beam is transported to the irradiation apparatus 16 through the beam transportation system 15 and is irradiated to the cancer in the body of the patient lying on the treatment couch 17 from the irradiation apparatus 16.

Prior to describing the main feature of the present invention, i.e., the measurement of energy of the orbiting ion beam 14, the relationship of the energy of the ion beam 14 versus the bending magnetic field strength, the frequency, and the beam orbit will be briefly described below. The relationship expressed by Eq. (1) is approximately held between energy E and momentum p of the orbiting ion beam. In Eq. (1), c represents the velocity of light.

$$E \approx cp \qquad \text{Eq. (1)}$$

Also, an orbit displacement $\Delta x$ of the barycenter of the ion beam caused at the measurement position with a change of the momentum is expressed by Eq. (2) wherein $\Delta x$ represents the displacement of the ion beam orbit at the measurement position in the synchrotron 3 (i.e., the position in which the beam position monitor 20 is installed), and $\eta$ represents the dispersion function at the measurement position.

$$\Delta x = \eta \frac{\Delta p}{p} \qquad \text{Eq. (2)}$$

The momentum p and the bending magnetic field strength B are expressed by Eq. (3) based on the relationship of p=eBρ. In Eq. (3), e represents the charge amount and ρ represents the radius of bending of the ion beam 14 caused by the bending magnetic field.

$$\frac{\Delta p}{p} = e\rho \frac{\Delta B}{B} \qquad \text{Eq. (3)}$$

Thus, from the relationship between the momentum p and the bending magnetic field strength B, it is understood that, as expressed by Eq. (3), a change of the bending magnetic field strength causes a change of the momentum, and that, based on Eq. (2), a change of the bending magnetic field strength further causes the orbit displacement Δx of the barycenter of the ion beam as expressed by Eq. (4).

$$\Delta x = e\rho\eta \frac{\Delta B}{B} \qquad \text{Eq. (4)}$$

The revolution frequency f of the orbiting ion beam 14 can be given as a function of the bending magnetic field strength B, as expressed by Eq. (5) wherein h represents the number of bunches, R represents the average radius of the synchrotron 3, and $m_0$ represents the rest mass of an orbiting charged particle.

$$f = \frac{ch}{2\pi R}\left[1 + \left(\frac{m_0 c}{eB\rho}\right)^2\right]^{-\frac{1}{2}} \qquad \text{Eq. (5)}$$

Ion beam acceleration control in the synchrotron 3 is performed by controlling the revolution frequency of the ion beam 14 on the basis of the bending magnetic field strength B that has a low control response. The RF controller 24 for acceleration detects (though not shown) a change of the bending magnetic field strength and controls the frequency set in the RF oscillator 11 for acceleration. Therefore, if the bending magnetic field strength and the frequency of the RF voltage hold the relationship expressed by Eq. (5), the ion beam 14 circulates within the synchrotron 3 along the predetermined orbit. In other words, when the bending magnetic field strength defining the energy of the ion beam 14 and the frequency of the RF voltage applied to the ion beam 14 at the end of the acceleration hold the relationship expressed by Eq. (5), the ion beam orbit within the synchrotron 3 is kept constant. If the bending magnetic field strength or the frequency of the RF voltage is shifted and the ion beam 14 is accelerated in the state in which the relationship expressed by Eq. (5) is not held, the position of the ion beam orbit at the end of the acceleration is changed. Accordingly, there is a risk that the energy of the ion beam at the end of the acceleration may be not matched with the set energy.

The position of the ion beam orbit and the frequency of the RF voltage at the time when the ion beam 14 has been accelerated until the energy of the ion beam 14 reaches the set energy are measured by the beam position monitor 20 and the cavity voltage monitor 18, respectively. Upon passage of the ion beam 14, the beam position monitor 20 generates a voltage $V_L$ between one pair of electrodes 55A and 55B and a voltage $V_R$ between one other pair of electrodes 56A and 56B. By executing simple signal processing expressed by Eq. (6) using those voltages, the position x of the ion beam orbit at the position where the beam position monitor 20 is installed can be detected. In Eq. (6), W represents an electrode width of the beam position monitor 20.

$$x = \frac{W}{2}\frac{V_R - V_L}{V_R + V_L} \qquad \text{Eq. (6)}$$

A description is now made of the measurement of energy of the ion beam 14 performed in this embodiment. The signal processing based on Eq. (6) is executed in the beam signal processing unit 21 to which both the voltage $V_L$, $V_R$ are inputted. Also, the frequency of the RF voltage is measured in the frequency counter 19 by using a cavity voltage signal detected by the cavity voltage monitor 18. A practical example of the frequency counter 19 is a frequency counter, a spectrum analyzer, or a frequency-voltage converter.

A measured value Rmes of the radial beam position x obtained by the beam signal processing unit 21 and a measured value Fines of the frequency of the RF voltage (hereinafter referred to as the "acceleration frequency") obtained by the frequency counter 19 are inputted to the energy judgment processing unit 26. An energy judgment process executed in the energy judgment processing unit 26 will be described in more detail with reference to FIG. 3.

Figure 4B:
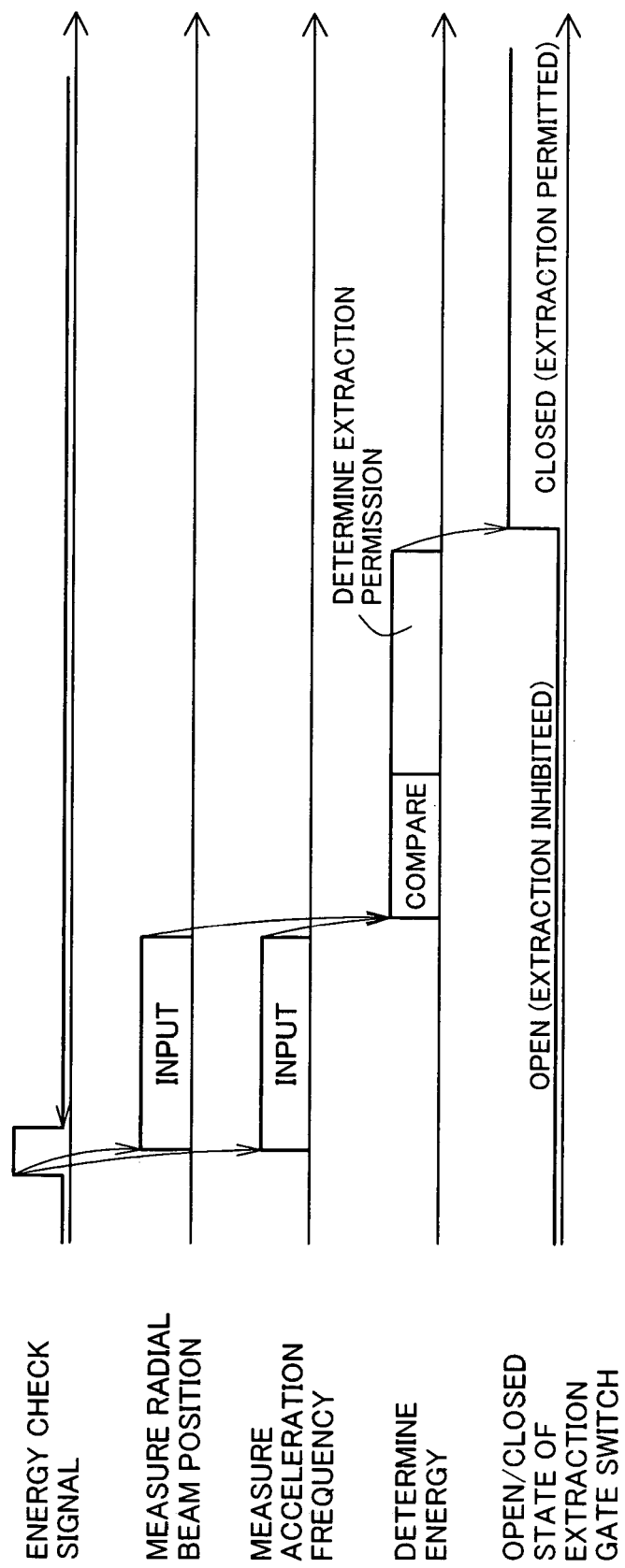

The energy judgment processing unit 26 receives the judgment information 78 corresponding to the set energy from the accelerator controller 22 (step 30). The judgment information 78 contains a reference value Rdes of the radial beam position x, an allowable range Rerr for the reference value Rdes, a reference value Fdes of the frequency of the RF voltage (i.e., the acceleration frequency), and an allowable range Ferr for the reference value Fdes at the end of the acceleration. At the time of energy check (see FIG. 4A) after the end of the acceleration, the energy judgment processing unit 26 receives the energy check signal 75 outputted from the timing controller 25 (step 31). After receiving the energy check signal 75, the energy judgment processing unit 26 receives the measured value Rmes of the radial beam position x from the beam signal processing unit 21 and the measured value Fines of the acceleration frequency from the frequency counter 19 (steps 32 and 33). The measured values Rmes and Fines represent respective values measured after the outputting of the energy check signal 75. Receiving the measured values Rmes and Fines after the energy judgment processing unit 26 has received the energy check signal 75 means that the radial beam position x and the acceleration frequency are measured after the outputting of the energy check signal 75 from the timing controller 25. In step 34, an absolute value of a deviation Rdev between the measured value Rmes and the reference value Rdes is calculated. In other words, Rdev=|Rmes−Rdes| is computed. In step 35, an absolute value of a deviation Fdev between the measured value Fines and the reference value Fdes is calculated. In other words, Fdev=|Fines−Fdes| is computed. Then, it is determined whether Rdev>Rerr is satisfied (step 36). If the determination in step 36 is "No", it is determined whether Fdev>Ferr is satisfied (step 37). If the determination result in step 37 is "No", it is determined that the energy of the ion beam 14 reaches the set energy and is normal (step 38). Correspondingly, an energy normal signal is outputted as an energy judgment signal 77 to the accelerator controller 22 and the gate switch 9 (step 39). The gate switch 9 is closed in response to the energy normal signal. The outputting of the energy normal signal means that the energy of the ion beam 14 after the end of the acceleration is matched with the set energy. If the determination result in step 36 or 37 is "Yes", it is determined that the energy of the ion beam 14 deviates from the set energy and is abnormal (step 40). Correspondingly, an energy abnormal signal is outputted as the energy judgment signal 77 to the accelerator controller 22 and the gate switch 9 (step 41). The outputting of the energy abnormal signal means that the energy of the ion beam 14 after the end of the acceleration deviates from the set energy. The gate switch 9 is closed when the energy normal signal is outputted, and it is opened when the energy abnormal signal is outputted. The outputting of the energy abnormal signal inhibits the application of the RF signal from the RF knockout electrode 6, to thereby stop the extraction of the ion beam from the synchrotron 3. After the end of step 38 or 39, the energy judgment processing unit 26 waits until the end of next acceleration (step 42). FIG. 4B shows the foregoing steps of the energy determination process together in the form of a time-serial chart.

In response to the energy normal signal or the energy abnormal signal, the accelerator controller 22 having received the energy judgment signal 77 monitors the state of the ion beam 14 being supplied to the irradiation apparatus 16.

When the gate switch 9 is closed in response to the energy normal signal outputted from the energy judgment processing unit 26 and the extraction switch 8 is closed in response to the outputting of the extraction permit signal 76, the ion beam 14 is extracted from the synchrotron 3 and irradiated to the cancer in the body of the patient in a manner as described above. On the other hand, in the state of the gate switch 9 being opened in response to the energy abnormal signal outputted from the energy judgment processing unit 26, even when the extraction switch 8 is closed in response to the outputting of the extraction permit signal 76, the ion beam is not extracted from the synchrotron 3 because no RF signal is applied to the RF knockout electrode 6.

Figure 5:
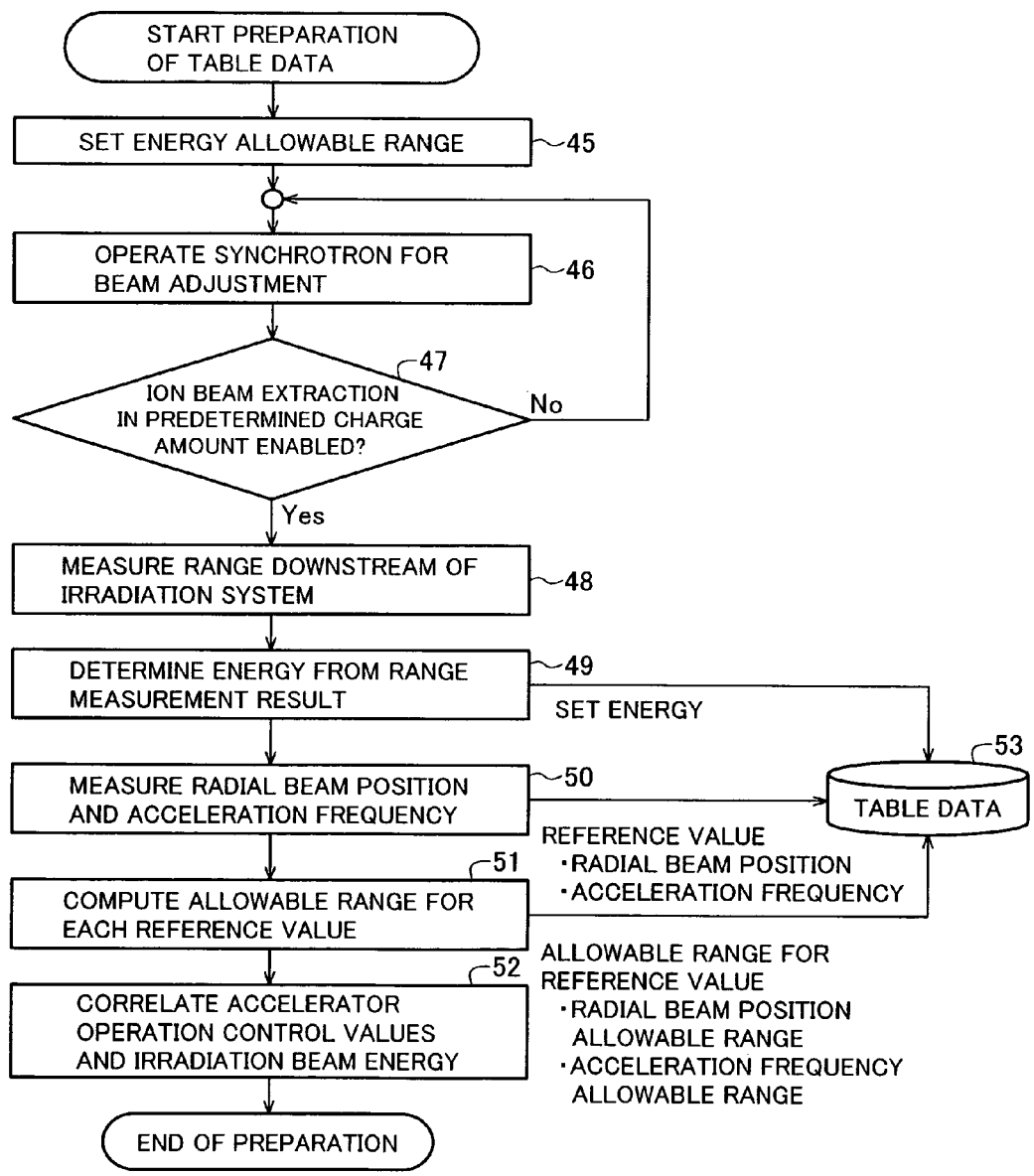
FIG. 5 is a flowchart for explaining preparation of judgment information.

Steps for preparing the judgment information 78 used in the energy determination process executed in the energy judgment processing unit 26 will be described below with reference to FIG. 5. First, an allowable range of energy variations is set (step 45). This allowable range is set to be, e.g., not larger than ±0.1% of the set energy when the ion beam is irradiated based on the ion beam scanning method. The allowable range of energy variations differs depending on the set energy and is decided as a setting parameter for the particle therapy system 1 beforehand. Then, an operation for adjustment of the ion beam is performed in the synchrotron 3 (step 46). In this adjustment operation, the acceleration frequency is adjusted with respect to the bending magnetic field strength so that the ion beam 14 is accelerated to reach the set energy, and the amount of excitation for each of the magnets disposed in the synchrotron 3, the acceleration frequency, etc. are adjusted so that the ion beam can be extracted in a predetermined charge amount from the synchrotron 3.

After the end of the above-described adjustment, it is determined whether the ion beam can be extracted in the predetermined charge amount (step 47). If the determination result is "No", the adjustment operation in step 46 is performed again to adjust the amount of excitation for each of the magnets disposed in the synchrotron 3, the acceleration frequency, etc. If the determination result in step 47 is "Yes", the ion beam is transported to the irradiation apparatus 16, and the range of the ion beam having passed through the irradiation apparatus 16 is measured by a dose meter, e.g., a water phantom, installed downstream of the irradiation apparatus 16 (step 48). Based on the measured result of the range, the energy of the ion beam accelerated and extracted from the synchrotron 3 is determined (step 49).

The frequency of the RF voltage applied to the RF cavity 10 (i.e., the acceleration frequency) and the position of the ion beam orbit at the end of acceleration of the ion beam are measured (step 50). The reference values of both the acceleration frequency and the orbit position of the barycenter of the ion beam are given by respective values measured in the above measuring steps. Then, respective allowable ranges for the reference values of the acceleration frequency and the radial beam position are calculated (step 51). Table data corresponding to one level of energy is prepared using the energy of the extracted ion beam which has been judged in step 49, the respective reference values of the acceleration frequency and the radial beam position which have been measured in step 50, and the respective allowable ranges for those reference values which have been calculated in step 51 (step 53). Finally, a set of operation control values for the synchrotron 3, the measured results of the ion beam energy, and the table data are correlated with one another, thereby preparing acceleration control pattern data for the synchrotron 3 (step 52). The above-described processing is repeatedly executed while changing the energy of the ion beam extracted from the synchrotron 3 to each of various levels, to thereby obtain the respective reference values of the acceleration frequency and the radial beam position, as well as the respective allowable ranges for those reference values corresponding to each different level of energy. The respective reference values of the acceleration frequency and the radial beam position, as well as the respective allowable ranges for those reference values, which have been obtained in the processing shown in FIG. 5, are used as the judgment information 78 in the process for determining the ion beam energy.

With this embodiment, whether the energy of the ion beam 14 orbiting within the synchrotron 3 is matched with the set energy can be confirmed by using the acceleration frequency and the radial beam position in the state where the ion beam 14 can be extracted from the accelerator, but before the irradiation of the ion beam 14 to the patient (i.e., in the state after the end of acceleration of the ion beam). Therefore, the ion beam 14 at the level of the set energy can be irradiated to the patient, and the position in the patient body where the ion beam 14 reaches (i.e., the position where the Bragg peak is formed) can be prevented from deviating from the destination position of the ion beam set in the treatment plan (i.e., from the set destination position). In particular, the energy of the ion beam 14 can be confirmed after the end of acceleration of the ion beam 14, but before the irradiation of the ion beam 14 from the synchrotron 3. Further, since the gate switch 9 is opened when the energy of the ion beam 14 after the end of the acceleration differs from the set energy, the ion beam 14 having energy at a value different from the set energy can be prevented from being extracted from the synchrotron 3, namely it can be prevented from being irradiated to the patient. This remarkably increases safety of the particle therapy system 1. If the ion beam 14 having energy at a value different from the set energy is irradiated to the patient, the Bragg peak is formed in the position of normal cells other than the cancer, and the normal cells are severely damaged. In other words, this first embodiment is able to avoid damage of the normal cells, which could be caused by the ion beam 14 reaching the position deviated from the destination position.

Second Embodiment

Figure 6:
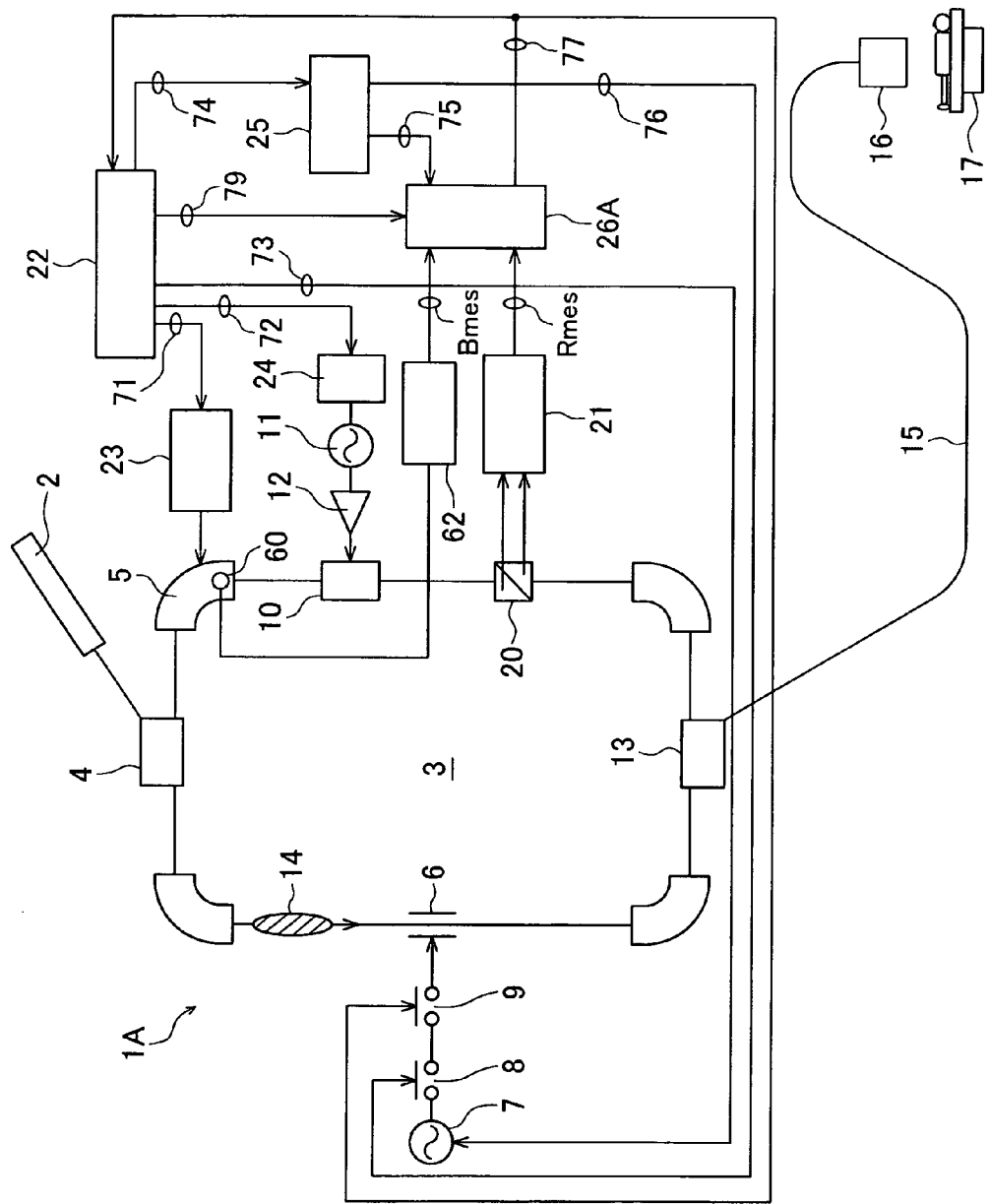
FIG. 6 is a block diagram of a particle therapy system according to another preferable embodiment, i.e., a second embodiment, of the present invention.

A particle therapy system 1A according to a second embodiment of the present invention will be described below with reference to FIG. 6. The particle therapy system 1A differs from the particle therapy system 1 of the first embodiment in using a magnetic field sensor 60, a bending magnetic field strength measuring unit 62, and an energy judgment processing unit 26A in place of the cavity voltage monitor 18, the frequency counter 19, and the energy judgment processing unit 26, respectively. The other construction of the particle therapy system 1A is the same as that of the particle therapy system 1. The magnetic field sensor 60 is installed on the bending magnet 5. The bending magnetic field strength measuring unit 62 connected to the magnetic field sensor 60 is connected to the energy judgment processing unit 26A. A practical example of the magnetic field sensor 60 is a sensor for detecting an absolute magnetic field, such as a Hall device, or a sensor for detecting an absolute magnetic field, such as a search coil (see Japanese Patent No. 3269437).

This embodiment uses, as the magnetic field sensor 60, a Hall device for detecting an absolute magnetic field. A detected signal from the magnetic field sensor 60 is inputted to the bending magnetic field strength measuring unit 62. The bending magnetic field strength measuring unit 62 measures the bending magnetic field strength based on the detected signal, and then outputs a measured value of the bending magnetic field strength to the energy judgment processing unit 26A. Using a measured value Bmes of the bending magnetic field strength and a measured value Rmes of the radial beam position x, the energy judgment processing unit 26A executes an energy determination process modified from the energy determination process shown in FIG. 3, to thereby determine whether the energy of the ion beam 14 orbiting within the synchrotron 3 at the end of the acceleration is matched with the set energy. The modified energy determination process differs from the energy determination process shown in FIG. 3 in replacing the reference value Fdes with a reference value Bdes of the bending magnetic field strength, the allowable range Ferr with an allowable range Berr for the reference value Bdes, and the measured value Fines with the measured value Bmes. Judgment information 79 transmitted from the accelerator controller 22 to the energy judgment processing unit 26A contains the reference value Rdes and the allowable range Rerr, as well as the reference value Bdes of the bending magnetic field strength and the allowable range Berr for the reference value Bdes at the end of the acceleration.

With this embodiment, whether the energy of the ion beam 14 orbiting within the synchrotron 3 is matched with the set energy can be confirmed by using the bending magnetic field strength and the radial beam position in the state where the ion beam 14 can be extracted from the accelerator, but before the irradiation of the ion beam 14 to the patient. Thus, this second embodiment can provide the advantages obtainable with the first embodiment.

Incidentally, an output voltage of a search coil represents a time-dependent change rate of the bending magnetic field strength. When measuring the bending magnetic field strength by using an output signal of a search coil instead of the Hall device, therefore, a change of the bending magnetic field strength in an acceleration control zone can be measured by installing, in the bending magnetic field strength measuring unit 62, a circuit for integrating the output voltage of the search oil.

Third Embodiment

Figure 7:
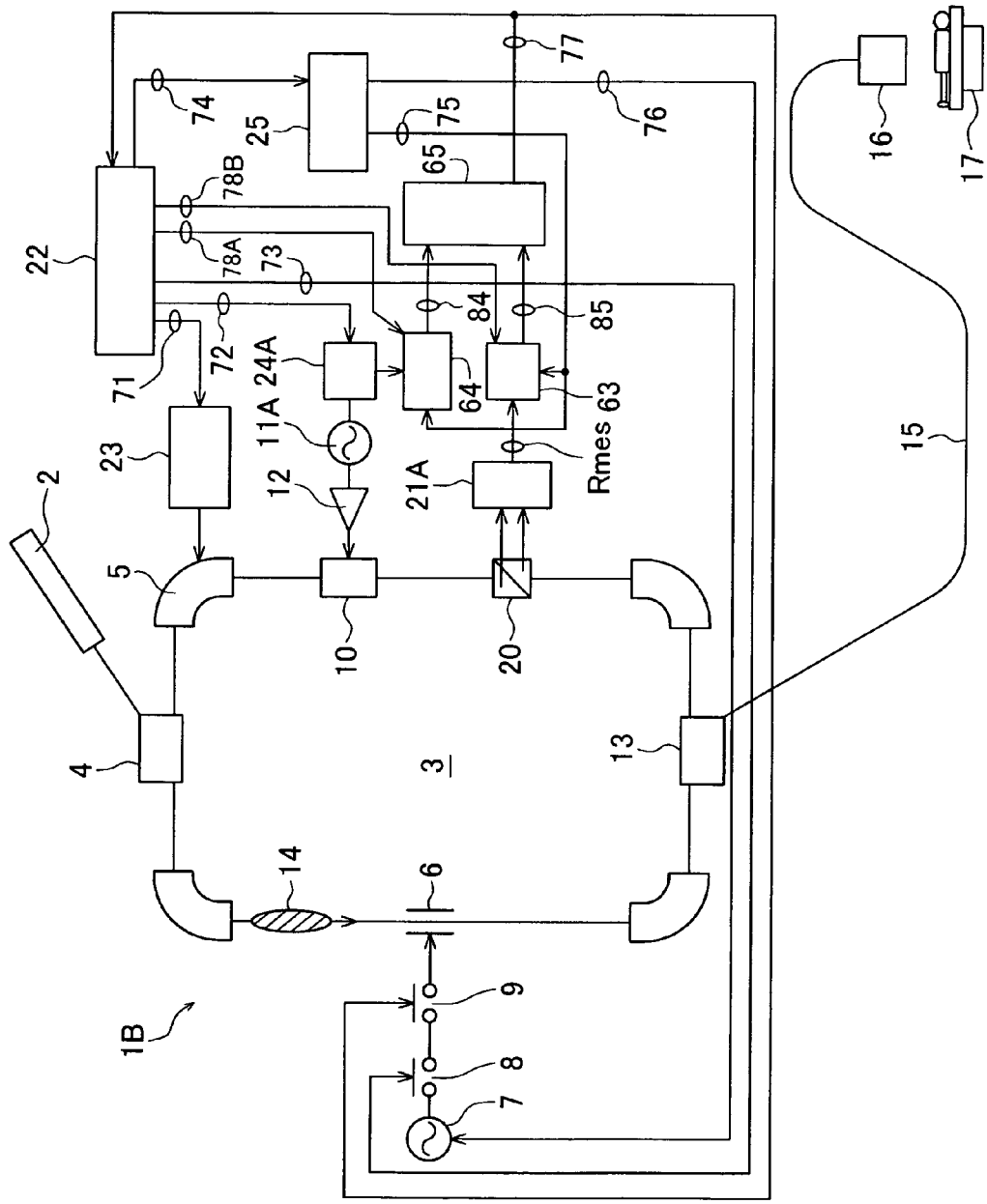
FIG. 7 is a block diagram of a particle therapy system according to still another preferable embodiment, i.e., a third embodiment, of the present invention.

A particle therapy system 1B according to a third embodiment of the present invention will be described below with reference to FIG. 7. The particle therapy system 1B of this third embodiment differs from the particle therapy system 1 of the first embodiment in that the cavity voltage monitor 18 and the frequency counter 19 are omitted, and the energy judgment processing unit 26 is replaced with a radial beam position judgment unit 63, a frequency judgment unit 64, and a judgment result output unit 65. The other construction of the particle therapy system 1B is the same as that of the particle therapy system 1. The radial beam position judgment unit 63, the frequency judgment unit 64, and the judgment result output unit judgment result output unit 65 essentially constitute the energy judgment processing unit 26.

With recent progress of the digital technology, the RF controller and the beam signal processing unit are constructed of a digital signal processing circuit using a DSP (Digital Signal Processor), etc. in many cases. This embodiment employs, instead of the RF controller 24 in the first embodiment, an RF controller 24A including a digital signal processing circuit using a DSP, and instead of the beam signal processing unit 21, a beam signal processing unit (radial beam position measuring device) 21A including a digital signal processing circuit using a DSP. The frequency judgment unit 64 is connected to the RF controller 24A. The radial beam position judgment unit 63 is connected to the beam signal processing unit 21A. Because of employing the RF controller 24A, a digital oscillator 11A is employed as the oscillator for generating the RF voltage applied to the RF cavity, whereby an RF signal is produced with high purity and high reproducibility. Further, the frequency of the RF signal outputted from the digital oscillator 11A is set with a digital value from the RF controller 24A and is outputted from the oscillator with high fidelity. Accordingly, with no need of utilizing any frequency counter, such as a spectrum analyzer, to measure the output signal from the cavity voltage monitor associated with the RF cavity, a similar result to that in the case of externally measuring the frequency can be obtained by confirming the frequency of the RF voltage set for the digital oscillator 11A.

Figure 3:
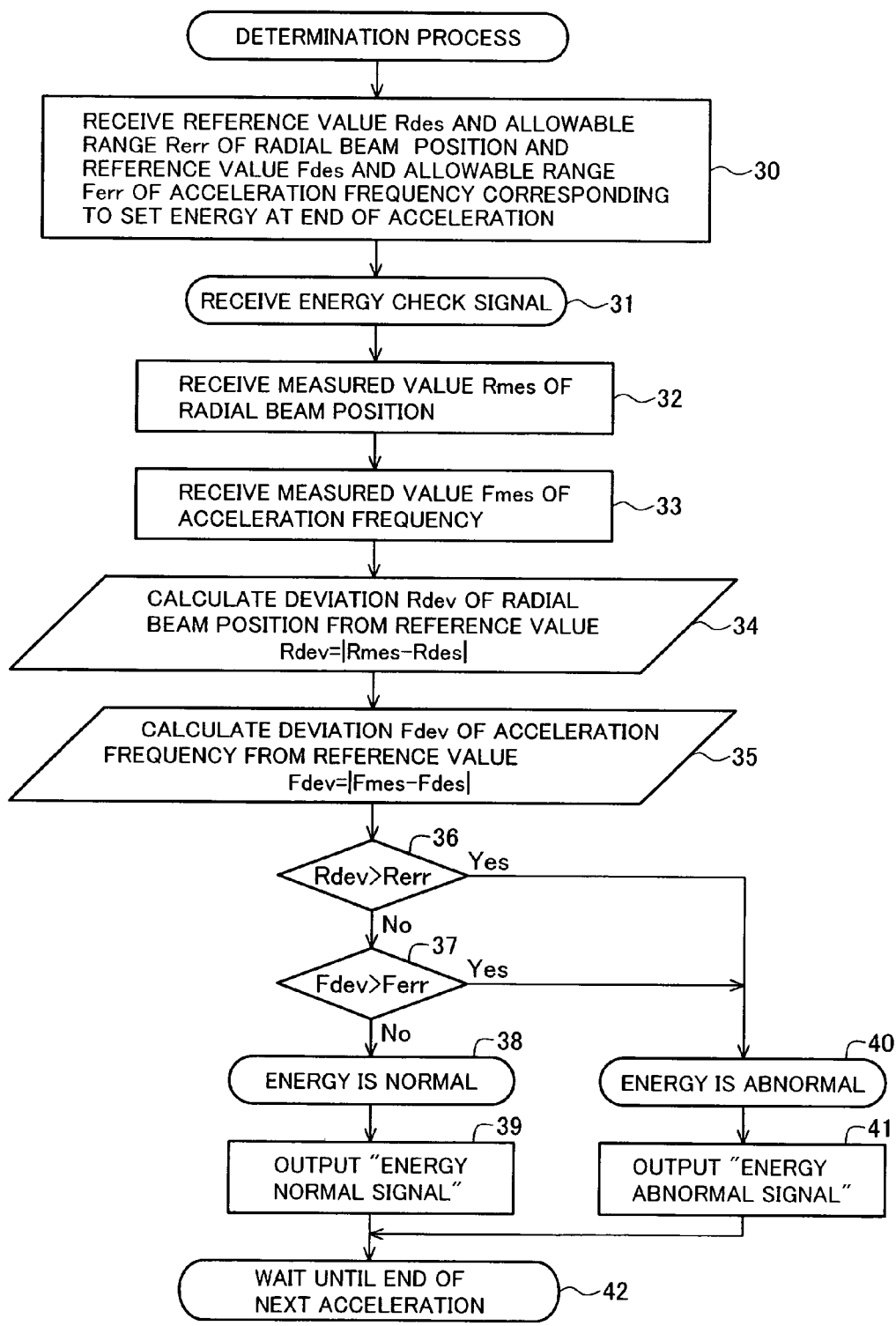
FIG. 3 is a flowchart for explaining processing executed by an energy judgment processing unit in FIG. 2.

The frequency judgment unit 64 executes the processing of steps 30, 31, 33, 35 and 37 in the energy determination process shown in FIG. 3. In step 30, the frequency judgment unit 64 receives the reference value Fdes and the allowable range Ferr, i.e., judgment information 78A corresponding to the set energy, from the accelerator controller 22. Then, the frequency judgment unit 64 executes the processing of steps 31, 33, 35 and 37. In step 33, however, the frequency judgment unit 64 receives the frequency set for the digital oscillator 11A, as the measured value Fines, from the RF controller 24A. The radial beam position judgment unit 63 executes the processing of steps 30-32, 34 and 36 in the energy determination process shown in FIG. 3. In step 30, the radial beam position judgment unit 63 receives the reference value Rdes and the allowable range Rerr, i.e., judgment information 78B corresponding to the set energy, from the accelerator controller 22. Then, the radial beam position judgment unit 63 executes the processing of steps 31, 32, 34 and 36.

The judgment result output unit 65 receives judgment result 85 obtained in step 36 from the radial beam position judgment unit 63 and judgment result 84 obtained in step 37 from the frequency judgment unit 64. If both results of the judgment result 84, 85 represent "No", the judgment result output unit 65 executes the processing of steps 38, 39 shown in FIG. 3 and outputs, as the energy judgment signal 77, the energy normal signal to the accelerator controller 22 and the gate switch 9. If the judgment result 84 or the judgment result 85 represents "Yes", the judgment result output unit 65 executes the processing of steps 40, 41 shown in FIG. 3 and outputs, as the energy judgment signal 77, the energy abnormal signal to the accelerator controller 22 and the gate switch 9.

This third embodiment can also provide the advantages obtainable with the first embodiment.

Fourth Embodiment

Figure 8:
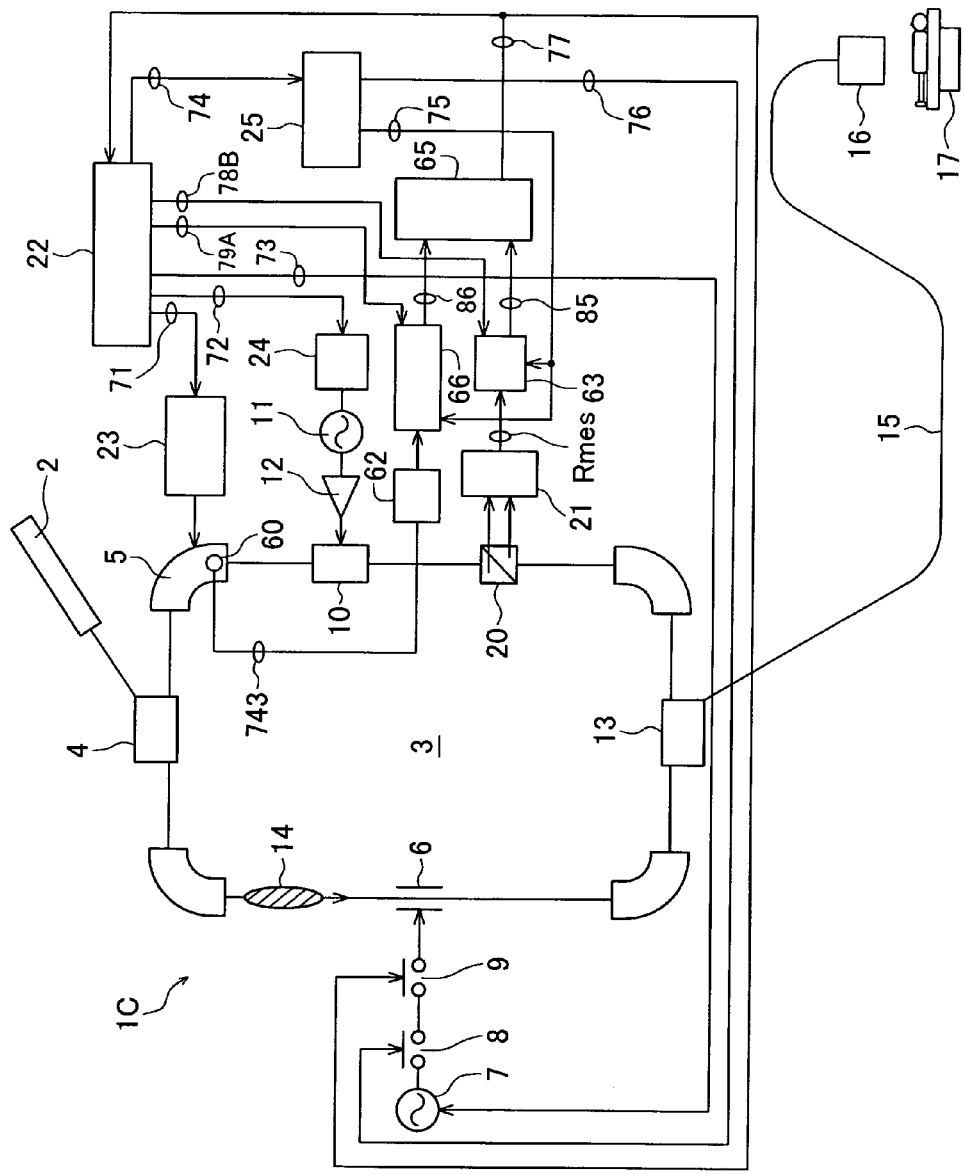
FIG. 8 is a block diagram of a particle therapy system according to still another preferable embodiment, i.e., a fourth embodiment, of the present invention.

A particle therapy system 1C according to a fourth embodiment of the present invention will be described below with reference to FIG. 8. The particle therapy system 1C of this fourth embodiment differs from the particle therapy system 1A of the second embodiment in that the energy judgment processing unit 26A is replaced with a radial beam position judgment unit 63, a bending magnetic field strength judgment unit 66, and a judgment result output unit 65. The other construction of the particle therapy system 1C is the same as that of the particle therapy system 1A. The radial beam position judgment unit 63, the bending magnetic field strength judgment unit 66, and the judgment result output unit 66 essentially constitute the energy judgment processing unit 26A. The bending magnetic field strength judgment unit 66 is connected to the bending magnetic field strength meter 62.

The bending magnetic field strength judgment unit 66 executes the processing of steps 30, 31, 33, 35 and 37 in the modified energy determination process described in the second embodiment. In step 30., the bending magnetic field strength judgment unit 66 receives the reference value Bdes and the allowable range Berr, i.e., judgment information 79A corresponding to the set energy, from the accelerator controller 22. Then, the bending magnetic field strength judgment unit 66 executes the processing of steps 31, 33, 35 and 37. The radial beam position judgment unit 63 executes the processing of steps 30-32, 34 and 36 in the modified energy determination process described in the second embodiment. In step 30, the radial beam position judgment unit 63 receives the reference value Rdes and the allowable range Rerr, i.e., the judgment information 78B corresponding to the set energy, from the accelerator controller 22. Then, the radial beam position judgment unit 63 executes the processing of steps 31, 32, 34 and 36.

The judgment result output unit 65 receives the judgment result 85 obtained in step 36 from the radial beam position judgment unit 63 and judgment result 86 obtained in step 37 from the bending magnetic field strength judgment unit 66. If both results of the judgment result 85, 86 represent "No", the judgment result output unit 65 executes the processing of steps 38, 39 and outputs, as the energy judgment signal 77, the energy normal signal to the accelerator controller 22 and the gate switch 9. If the judgment result 85 or the judgment result 86 represents "Yes", the judgment result output unit 65 executes the processing of steps 40, 41 and outputs, as the energy judgment signal 77, the energy abnormal signal to the accelerator controller 22 and the gate switch 9.

This fourth embodiment can also provide the advantages obtainable with the second embodiment.

Fifth Embodiment

Figure 9:
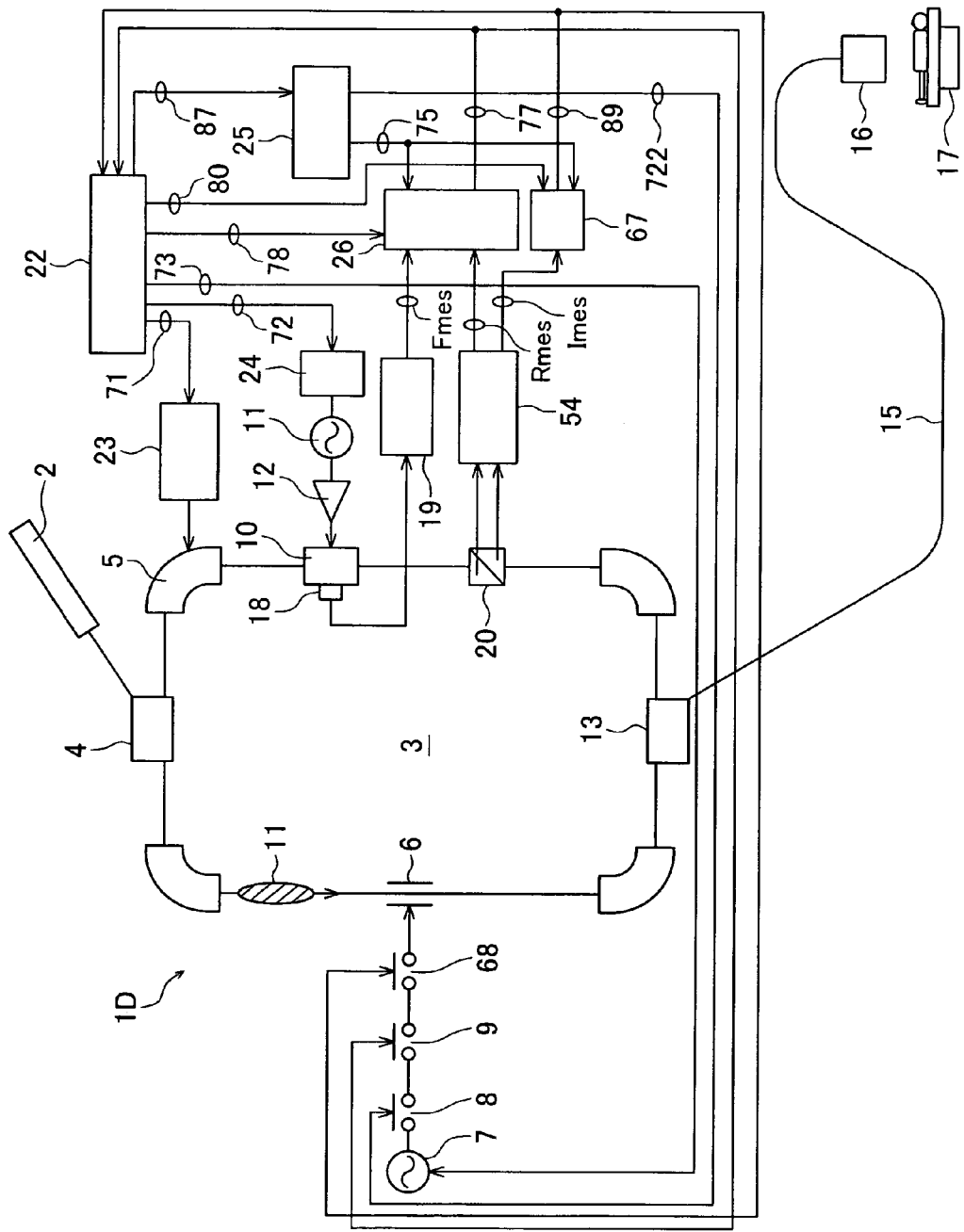
FIG. 9 is a block diagram of a particle therapy system according to still another preferable embodiment, i.e., a fifth embodiment, of the present invention.

A particle therapy system 1D according to a fifth embodiment of the present invention will be described below with reference to FIG. 9. The particle therapy system 1D of this fifth embodiment is constituted by adding, to the particle therapy system 1 of the first embodiment, a beam intensity judgment unit 67 and a gate switch (third on/off switch) 68 serving as a second safety device. Further, the particle therapy system iD includes a beam signal processing unit 54. The other construction of the particle therapy system iD is the same as that of the particle therapy system 1. The gate switch 68 is disposed between the RF knockout electrode 6 and the gate switch 9, and it is connected to them. The beam signal processing unit 54 is connected to the two sets of electrodes (i.e., the, electrodes 68A, 68B and the electrodes 69A, 69B) of the beam position monitor 20. The beam intensity judgment unit 67 is connected to an envelope detector 55 (described later) of the beam signal processing unit 54, the accelerator controller 22, the timing controller 25, and the gate switch 68. The beam intensity judgment unit 67 is provided separately from the energy judgment processing unit 26.

Figure 10:
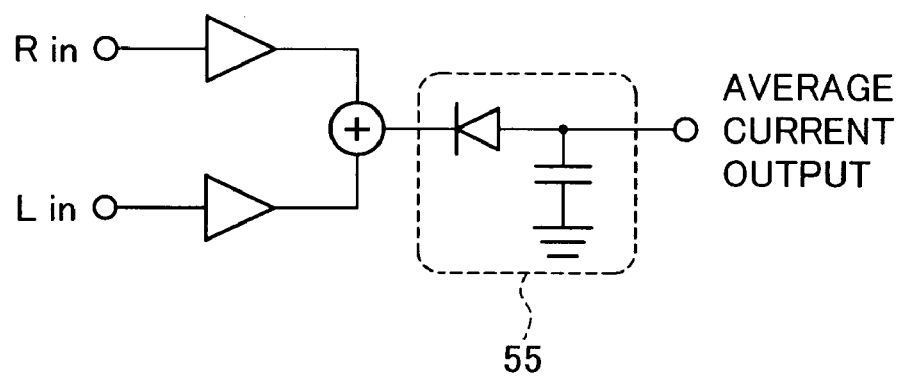
FIG. 10 is a diagram of an envelope detection circuit provided in a beam signal processing unit in FIG. 9.
Figure 11:
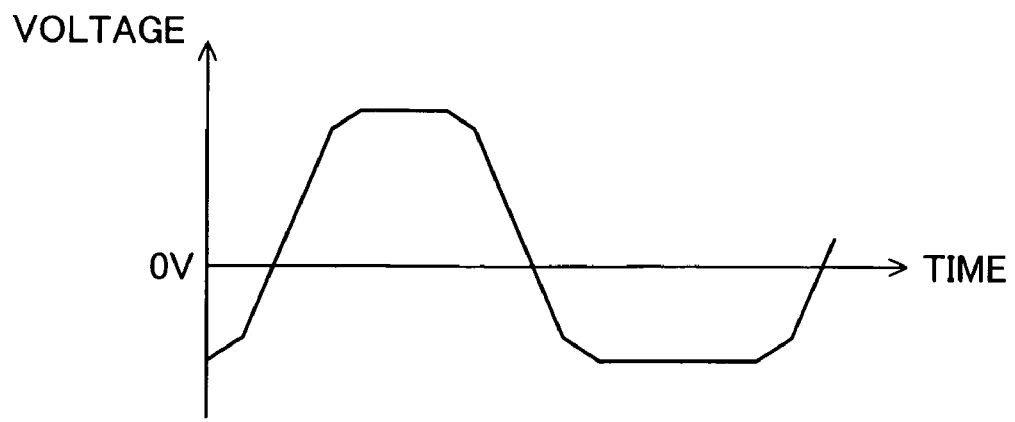
FIG. 11 is a graph for explaining the waveform of a signal outputted from a beam position monitor in FIG. 9.

The strength of the ion beam orbiting within the synchrotron 3 can be measured as an average charge amount by envelope detection of signals outputted from the two sets of electrodes (i.e., the electrodes 68A, 68B and the electrodes 69A, 69B) of the beam position monitor 20. The beam signal processing unit 54 includes the beam signal processing unit 21 (not shown in FIG. 9), which is used in the first embodiment, and the envelope detector 55 (see FIG. 10) for performing the envelope detection. The beam signal processing unit 21 and the envelope detector 55 are connected to the two sets of electrodes of the beam position monitor 20. The beam position monitor 20 outputs a signal having a voltage waveform shown in FIG. 11. Such a voltage waveform is provided as the sum of outputs from the two sets of electrodes and is inputted to both of the beam signal processing unit 21 and the envelope detector 55. The voltage waveform represents the form of the bunched ion beam 14 orbiting within the synchrotron 3. Because the average charge amount, i.e., the ion beam intensity, is detected as a DC component on the negative side of the bunched waveform, it can be obtained by adding respective signals ($V_R$, $V_L$) outputted from the two sets of electrodes of the beam position monitor 20, and performing the envelope detection of a negative component of the added result in the envelope detector 55. A measured value Imes of the ion beam intensity obtained by the envelope detector 55 is inputted to the beam intensity judgment unit 67.

As in the first embodiment, the energy judgment processing unit 26 receives the measured value Rmes from the beam signal processing unit 21 and the measured value Fines from the frequency counter 19. Then, the energy judgment processing unit 26 executes the determination process shown in FIG. 3, and outputs the energy normal signal or the energy abnormal signal to the accelerator controller 22 and the gate switch 9.

A process for determining the ion beam intensity, executed by the beam intensity judgment unit 67, will be described below. First, the beam intensity judgment unit 67 receives, from the accelerator controller 22, a reference value Vdes of the ion beam intensity corresponding to the set ion beam intensity that has been decided as judgment information 80 in a treatment plan, and an allowable range Verr for the reference value Vdes. After receiving the energy check signal 75, the beam intensity judgment unit 67 receives the measured value Imes measured after the outputting of the energy check signal 75. An absolute value of a deviation Idev between the measured value Imes and the reference value Ides is calculated. In other words, Idev=|Imes−Ides| is computed. Then, it is determined whether Idev>Ierr is satisfied. If this determination is "No", it is determined that the strength of the ion beam 14 reaches the set ion beam energy and is normal. Correspondingly, a strength normal signal is outputted as an ion beam intensity determination signal 89 to the accelerator controller 22 and the gate switch 68. The gate switch 68 is closed in response to the strength normal signal. The outputting of the strength normal signal means that the energy of the ion beam 14 after the end of the acceleration is matched with the set energy. If the above determination result is "Yes", this means that the strength of the ion beam 14 is in an abnormal state deviating from the set ion beam intensity. Therefore, a strength abnormal signal is outputted as the ion beam intensity determination signal 89 to the accelerator controller 22 and the gate switch 68. The gate switch 68 is closed when the strength normal signal is outputted, and it is opened when the strength abnormal signal is outputted. The outputting of the strength abnormal signal inhibits the application of the RF signal from the RF knockout electrode 6, to thereby stop the extraction of the ion beam from the synchrotron 3.

This fifth embodiment can provide the advantages obtainable with the first embodiment. In addition, this fifth embodiment can provide the following advantages. Since the strength of the ion beam 14 orbiting within the synchrotron 3 can be measured in accordance with the output of the beam position monitor 20 disposed in the synchrotron 3 after the end of the acceleration, but before the extraction of the ion beam 14, the strength of the ion beam 14 irradiated to the patient can be confirmed in advance. Therefore, the ion beam 14 having the set ion beam intensity can be irradiated to the cancer (target area) in the patient body. Particularly, in the case of dividing the target area into a plurality of layers in the direction of depth and irradiating the ion beam 14 for each of the divided layers, when the ion beam 14 is irradiated to one layer at a deep position, the ion beam is also irradiated to another layer at apposition shallower than that of the one layer. For that reason, it is required to reduce the strength of the ion beam irradiated to an area in the other layer at the shallower position, which overlies the one layer at the deep position. Even in such a case, with this fifth embodiment, whether the strength of the ion beam irradiated to the other layer is matched with the set ion beam intensity corresponding to the other layer can be confirmed in the state where the ion beam can be extracted from the accelerator, but before the irradiation of the ion beam 14 to the patient. If the ion beam intensity deviates from the set ion beam intensity, it is possible to inhibit the extraction of the ion beam from the accelerator, and to prevent the ion beam from being irradiated to the patient.

Thus, whether the energy and strength of the ion beam are matched with the set energy and strength of the ion beam can be confirmed after the end of acceleration of the ion beam, but before the irradiation of the ion beam to the patient. If at least one of the energy and strength of the ion beam is in an abnormal state, the irradiation of that ion beam to the patient can be avoided.

The beam intensity judgment unit 67, the gate switch 68, and the beam signal processing unit 54 used in this fifth embodiment are also applicable to any of the second to fourth embodiments described above. In the third embodiment, however, the beam signal processing unit 54 includes the beam signal processing unit 21A instead of the beam signal processing unit 21.

What is claimed is:

1. A particle therapy system comprising:
a circular accelerator for accelerating a charged particle beam, said circular accelerator including a cavity for applying a radio frequency wave to accelerate the charged particle beam;
a charged particle beam irradiation apparatus for irradiating the charged particle beam extracted from said circular accelerator to an irradiation target;
a frequency counter for measuring the frequency of said radio frequency wave applied by said cavity to accelerate the charged particle beam or the revolution frequency of the charged particle beam orbiting within said circular accelerator;
a radial beam position measuring device for measuring the orbit position of the charged particle beam orbiting within said circular accelerator; and
an energy determination device for determining energy of the charged particle beam orbiting within said circular accelerator after the end of acceleration of the charged particle beam by said circular accelerator and before extraction of the charged particle beam from said circular accelerator, and wherein said energy determination device determines the energy of the charged particle beam orbiting within said circular accelerator based on the frequency of the radio frequency wave or the revolution frequency of the charged particle beam measured by said frequency counter after the end of the acceleration, and the orbit position of the charged particle beam measured by said radial beam position measuring device after the end of the acceleration.

2. A particle therapy system comprising:
a circular accelerator for accelerating a charged particle beam, said circular accelerator including a bending magnet;
a charged particle beam irradiation apparatus for irradiating the charged particle beam extracted from said circular accelerator to an irradiation target;
a bending magnetic field strength measuring device for measuring the strength of the bending magnetic field of said bending magnet;
a radial beam position measuring device for measuring the orbit position of the charged particle beam orbiting within said circular accelerator; and
an energy determination device for determining energy of the charged particle beam orbiting within said circular accelerator after the end of acceleration of the charged particle beam by said circular accelerator and before extraction of the charged particle beam from said circular accelerator, and wherein said energy determination device determines the energy of the charged particle beam orbiting within said circular accelerator based on the strength of the bending magnetic field of the bending magnet measured by said bending magnetic field strength measuring device after the end of the acceleration and the orbit position of the charged particle beam measured by said radial beam position measuring device after the end of the acceleration.

3. A particle therapy system comprising:
a circular accelerator for accelerating a charged particle beam, said circular accelerator including a cavity for applying a radio frequency wave to accelerate the charged particle beam, and a bending magnet;
a charged particle beam irradiation apparatus for irradiating the charged particle beam extracted from said circular accelerator to an irradiation target;
a bending magnetic field strength measuring device for measuring the strength of the bending magnetic field of said bending magnet;
a frequency counter for measuring the frequency of said radio frequency wave applied by said cavity to accelerate the charged particle beam or the revolution frequency of the charged particle beam orbiting within said circular accelerator; and
an energy determination device for determining energy of the charged particle beam orbiting within said circular accelerator after the end of acceleration of the charged particle beam by said circular accelerator and before extraction of the charged particle beam from said circular accelerator, and wherein said energy determination device determines the energy of the charged particle beam orbiting within said circular accelerator based on the strength of the bending magnetic field of the bending magnet measured by said bending magnetic field strength measuring device after the end of the acceleration and the frequency of the radio frequency wave or the revolution frequency of the charged particle beam measured by said frequency counter after the end of the acceleration.

4. A particle therapy system according to claim 1, wherein said energy determination device determines that the energy of the charged particle beam orbiting within said circular accelerator after the end of the acceleration is normal, when the frequency of said radio frequency wave or the revolution frequency of the charged particle beam orbiting within said circular accelerator measured by said frequency counter after the end of the acceleration is within a first allowable range and the orbit position of the charged particle beam orbiting within said circular accelerator measured by said radial beam position measuring device after the end of the acceleration is within a second allowable range.

5. A particle therapy system according to claim 1, wherein said energy determination device determines that the energy of the charged particle beam orbiting within said circular accelerator after the end of the acceleration is abnormal, when the frequency of said radio frequency wave or the revolution frequency of the charged particle beam orbiting within said circular accelerator measured by said frequency counter after the end of the acceleration is outside a first allowable range or the orbit position of the charged particle beam orbiting within said circular accelerator measured by said radial beam position measuring device after the end of the acceleration is outside a second allowable range.

6. A particle therapy system according to claim 2, wherein said energy determination device determines that the energy of the charged particle beam orbiting within said circular accelerator after the end of the acceleration is normal, when the strength of the bending magnetic field of said bending magnet measured by said bending magnetic field strength measuring device after the end of the acceleration is within a first allowable range and an orbit position of the charged particle beam orbiting within said circular accelerator measured by said radial beam position measuring device after the end of the acceleration is within a second allowable range.

7. A particle therapy system according to claim 2, wherein said energy determination device determines that the energy of the charged particle beam orbiting within said circular accelerator after the end of the acceleration is abnormal, when the strength of the bending magnetic field of said bending magnet measured by said bending magnetic field strength measuring device after the end of the acceleration is outside a first allowable range or the orbit position of the charged particle beam orbiting within said circular accelerator measured by said radial beam position measuring device after the end of the acceleration is outside a second allowable range.

8. A particle therapy system according to any one of claims 1 to 3, further comprising a beam intensity determination device for determining beam intensity of the charged particle beam orbiting within said circular accelerator after the end of acceleration of the charged particle beam by said circular accelerator.

9. A particle therapy system according to claim 8, wherein said beam intensity determination device determines that the beam intensity of the charged particle beam orbiting within said circular accelerator after the end of the acceleration is normal, when the beam intensity is within a third allowable range.

10. A particle therapy system according to claim 8, wherein said beam intensity determination device determines that the beam intensity of the charged particle beam orbiting within said circular accelerator after the end of the acceleration is abnormal, when the beam intensity is outside a third allowable range.

11. A particle therapy system according to any one of claims 1 to 3, further comprising a first safety device for permitting extraction of the charged particle beam from said circular accelerator when said energy determination device determines that the energy of the charged particle beam orbiting within said circular accelerator is normal, and for inhibiting extraction of the charged particle beam from said circular accelerator when said energy determination device determines that the energy of the orbiting charged particle beam is abnormal.

12. A particle therapy system according to claim 8, further comprising a second safety device for permitting extraction of the charged particle beam from said circular accelerator when said beam intensity determination device determines that the beam intensity of the charged particle beam orbiting within said circular accelerator is normal, and for inhibiting extraction of the charged particle beam from said circular accelerator when said beam intensity determination device determines that the beam intensity of the orbiting charged particle beam is abnormal.

13. A particle therapy system according to claim 4, further comprising a first safety device for permitting extraction of the charged particle beam from said circular accelerator when said energy determination device determines that the energy of the charged particle beam orbiting within said circular accelerator is normal.

14. A particle therapy system according to claim 5, further comprising a first safety device for inhibiting extraction of the charged particle beam from said circular accelerator when said energy determination device determines that the energy of the charged particle beam orbiting within said circular accelerator is abnormal.

15. A particle therapy system according to claim 9, further comprising a second safety device for permitting extraction of the charged particle beam from said circular accelerator when said beam intensity determination device determines that the beam intensity of the charged particle beam orbiting within said circular accelerator is normal.

16. A particle therapy system according to claim 10, further comprising a second safety device for inhibiting extraction of the charged particle beam from said circular accelerator when said beam intensity determination device determines that the beam intensity of the charged particle beam orbiting within said circular accelerator is abnormal.

17. A particle therapy system according to claim 6, further comprising a first safety device for permitting extraction of the charged particle beam from said circular accelerator when said energy determination device determines that the energy of the charged particle beam orbiting within said circular accelerator is normal.

18. A particle therapy system according to claim 7, further comprising a first safety device for inhibiting extraction of the charged particle beam from said circular accelerator when said energy determination device determines that the energy of the charged particle beam orbiting within said circular accelerator is abnormal.

19. A particle therapy system according to claim 3, wherein said energy determination device determines that the energy of the charged particle beam orbiting after the end of the acceleration is normal, when the strength of the bending magnetic field of said bending magnet measured by said bending magnetic field strength measuring device after the end of the acceleration is within a first allowable range and the frequency of said radio frequency wave or the revolution frequency of the charged particle beam orbiting within said circular accelerator measured by said frequency counter after the end of the acceleration is within a second allowable range.

20. A particle therapy system according to claim 3, wherein said energy determination device determines that the energy of the charged particle beam orbiting after the end of the acceleration is abnormal, when the strength of a bending magnetic field of said bending magnet measured by said bending magnetic field strength measuring device after the end of the acceleration is outside a first allowable range, or the frequency of said radio frequency wave or the revolution frequency of the charged particle beam orbiting within said circular accelerator measured by said frequency counter after the end of the acceleration is outside a second allowable range.

21. A method of extracting a charged particle beam comprising the steps of:
accelerating a charged particle beam within a circular accelerator;
determining energy of the charged particle beam orbiting within said circular accelerator after the end of acceleration of the charged particle beam by said circular accelerator and before extraction of the charged particle beam from said circular accelerator; and
extracting said charged particle beam from said circular accelerator after completion of said energy determination, and wherein said energy determination is carried out based on a frequency of a radio frequency wave applied for accelerating the charged particle beam by an accelerating cavity provided to said circular accelerator, or a revolution frequency of the charged particle beam orbiting within said circular accelerator, and an orbit position of the charged particle beam orbiting within said circular accelerator, the frequency of the radio frequency wave or the revolution frequency of the charged particle beam orbiting within said circular accelerator and the orbit position of the charged particle beam orbiting within said circular accelerator used for the energy determination being the value measured after the end of the acceleration.

22. A method of extracting a charged particle beam comprising the steps of:
accelerating a charged particle beam within a circular accelerator;
determining energy of the charged particle beam orbiting within said circular accelerator after the end of acceleration of the charged particle beam by said circular accelerator and before extraction of the charged particle beam from said circular accelerator; and
extracting said charged particle beam from said circular accelerator after completion of said energy determination, and wherein said energy determination is carried out based on a strength of a bending magnetic field of a bending magnet provided to said circular accelerator and an orbit position of the charged particle beam orbiting within said circular accelerator, the strength of the bending magnetic field of the bending magnet and the orbit position of the charged particle beam orbiting within said circular acceleratator used for the energy determination being the values measured after the end of the acceleration.

23. A method of extracting a charged particle beam comprising the steps of:
accelerating a charged particle beam within a circular accelerator;
determining energy of the charged particle beam orbiting within said circular accelerator after the end of acceleration of the charged particle beam by said circular accelerator and before extraction of the charged particle beam from said circular accelerator; and
extracting said charged particle beam from said circular accelerator after completion of said energy determination, and wherein said energy determination is carried out based on a strength of a bending magnetic field of a bending magnet provided to said circular accelerator and a frequency of a radio frequency wave applied for accelerating the charged particle beam by an accelerating cavity provided to said circular accelerator, or a revolution frequency of the charged particle beam orbiting within said circular accelerator, the strength of the bending magnetic field of the bending magnet and the frequency of the radio frequency wave or the revolution frequency of the charged particle beam orbiting within said circular accelerator used for the energy determination being the values measured after the end of the acceleration.

24. A method of extracting a charged particle beam according to any one of claims 21 to 23 further comprising the step of permitting extraction of the charged particle beam from said circular accelerator when in said energy determination, it is determined that the energy of the orbiting charged particle beam is normal.

25. A method of extracting a charged particle beam according to any one of claims 21 to 23, further comprising the step of permitting extraction of the charged particle beam from said circular accelerator when in said energy determination, it is determined that a beam intensity of the orbiting charged particle beam is normal.

26. A particle therapy system according to claim 1, further comprising table data in which the energy of the charged particle beam determined beforehand by measurement is correlated with the frequency of the radio frequency wave applied for accelerating the charged particle beam by the accelerating cavity provided to said circular accelerator, or the revolution frequency of the charged particle beam orbiting within said circular accelerator, and the orbit position of the charged particle beam orbiting within said circular accelerator, and
wherein said energy determination device obtains from said table data the frequency of the radio frequency wave or the revolution frequency of the charged particle beam and the orbit position of the charged particle beam corresponding to a predetermined value of the energy of the charged particle beam, and determines whether the frequency of the radio frequency wave or the revolution frequency of the charged particle beam measured by said frequency counter after the end of the acceleration is within a first allowable range determined based on the frequency of the radio frequency wave or the revolution frequency of the charged particle beam obtained from said table data, and whether the orbit position of the charged particle beam measured by said radial beam position measuring device after the end of the acceleration is within a second allowable range determined based on the orbit position of the charged particle beam obtained from said table data.

27. A particle therapy system according to claim 1, further comprising table data in which the energy of the charged particle beam determined beforehand by measurement is correlated with the frequency of the radio frequency wave applied for accelerating the charged particle beam by the accelerating cavity provided to said circular accelerator, or the revolution frequency of the charged particle beam orbiting within said circular accelerator, and the orbit position of the charged particle beam orbiting within said circular accelerator, and wherein said energy determination device obtains from said table data the frequency of the radio frequency wave or the revolution frequency of the charged particle beam and the orbit position of the charged particle beam corresponding to a predetermined value of the energy of the charged particle beam, calculates a frequency deviation between the frequency of the radio frequency wave or the revolution frequency of the charged particle beam measured by said frequency counter after the end of the acceleration and the frequency of the radio frequency wave or the revolution frequency of the charged particle beam obtained from said table data and calculates an orbit position deviation between the orbit position of the charged particle beam measured by said radial beam position measuring device after the end of the acceleration and the orbit position of the charged particle beam obtained from said table data, and determines whether said frequency deviation and said orbit position deviation are within respective allowable ranges.

28. A particle therapy system according to claim 2, further comprising table data in which the energy of the charged particle beam determined beforehand by measurement is correlated with the strength of the bending magnetic field of the bending magnet provided to said circular accelerator and the orbit position of the charged particle beam orbiting within said circular accelerator, and wherein said energy determination device obtains from said table data the strength of the bending magnetic field of the bending magnet and the orbit position of the charged particle beam corresponding to a predetermined value of the energy of the charged particle beam, and determines whether the strength of the bending magnetic field of the bending magnet measured by said bending magnetic field strength measuring device after the end of the acceleration is within a first allowable range determined based on the strength of the bending magnetic field of the bending magnet obtained from said table data, and whether the orbit position of the charged particle beam measured by said radial beam position measuring device after the end of the acceleration is within a second allowable range determined based on the orbit position of the charged particle beam obtained from said table data.

29. A particle therapy system according to claim 2, further comprising table data in which the energy of the charged particle beam determined beforehand by measurement is correlated with the strength of the bending magnetic field of the bending magnet provided to said circular accelerator and the orbit position of the charged particle beam orbiting within said circular accelerator, and wherein said energy determination device obtains from said table data the strength of the bending magnetic field of the bending magnet and the orbit position of the charged particle beam corresponding to a predetermined value of the energy of the charged particle beam, calculates a magnetic field strength deviation between the strength of the bending magnetic field of the bending magnet measured by said bending magnetic field strength measuring device after the end of the acceleration and the strength of the bending magnetic field of the bending magnet obtained from said table data and calculates an orbit position deviation between the orbit position of the charged particle beam measured by said radial beam position measuring device after the end of the acceleration and the orbit position of the charged particle beam obtained from said table data, and determines whether said magnetic field strength deviation and said orbit position deviation are within respective allowable ranges.

30. A particle therapy system according to claim 3, further comprising table data in which the energy of the charged particle beam determined beforehand by measurement is correlated with the strength of the bending magnetic field of the bending magnet provided to said circular accelerator and the frequency of the radio frequency wave applied for accelerating the charged particle beam by the accelerating cavity provided to said circular accelerator, or the revolution frequency of the charged particle beam orbiting within said circular accelerator, and wherein said energy determination device obtains from said table data the strength of the bending magnetic field of the bending magnet and the frequency of the radio frequency wave or the revolution frequency of the charged particle beam corresponding to a predetermined value of the energy of the charged particle beam, and determines whether the strength of the bending magnetic field of the bending magnet measured by said bending magnetic field strength measuring device after the end of the acceleration is within a first allowable range determined based on the strength of the bending magnetic field of the bending magnet obtained from said table data, and whether the frequency of the radio frequency wave or the revolution frequency of the charged particle beam measured by said frequency counter after the end of the acceleration is within a second allowable range determined based on the frequency of the radio frequency wave or the revolution frequency of the charged particle beam obtained from said table data.

31. A particle therapy system according to claim 3, further comprising table data in which the energy of the charged particle beam determined beforehand by measurement is correlated with the strength of the bending magnetic field of the bending magnet provided to said circular accelerator and the frequency of the radio frequency wave applied for accelerating the charged particle beam by the accelerating cavity provided to said circular accelerator, or the revolution frequency of the charged particle beam orbiting within said circular accelerator, and wherein said energy determination device obtains from said table data the strength of the bending magnetic field of the bending magnet and the frequency of the radio frequency wave or the revolution frequency of the charged particle beam corresponding to a predetermined value of the energy of the charged particle beam, calculates a magnetic field strength deviation between the strength of the bending magnetic field of the bending magnet measured by said bending magnetic field strength measuring device after the end of the acceleration and the strength of the bending magnetic field of the bending magnet obtained from said table data and calculates a frequency deviation between the frequency of the radio frequency wave or the revolution frequency of the charged particle beam measured by said frequency counter after the end of the acceleration and the frequency of the radio frequency wave or the revolution frequency of the charged particle beam obtained from said table data, and determines whether said magnetic field strength deviation and said frequency are within respective allowable ranges.

* * * * *